(12) United States Patent
Outtrup et al.

(10) Patent No.: US 7,109,016 B2
(45) Date of Patent: Sep. 19, 2006

(54) SUBTILASE ENZYMES

(75) Inventors: Helle Outtrup, Værlose (DK); Poul Erik Pedersen, Søborg (DK); Marianne Vind Sørensen, Roskilde (DK)

(73) Assignee: Novozymes A/S, Bagsvaerd (DK)

( * ) Notice: Subject to any disclaimer, the term of this patent is extended or adjusted under 35 U.S.C. 154(b) by 2 days.

(21) Appl. No.: 09/931,701

(22) Filed: Aug. 16, 2001

(65) Prior Publication Data
US 2004/0241820 A1 Dec. 2, 2004

Related U.S. Application Data

(60) Provisional application No. 60/235,459, filed on Sep. 26, 2000.

(30) Foreign Application Priority Data
Aug. 21, 2000 (DK) ............... 2000 01232

(51) Int. Cl.
C12N 9/54 (2006.01)
C12N 15/57 (2006.01)
C12N 15/74 (2006.01)
C11D 3/386 (2006.01)

(52) U.S. Cl. ............ 435/221; 435/69.1; 435/252.3; 435/320.1; 435/471; 510/300; 536/23.2

(58) Field of Classification Search ............... 435/220, 435/221, 222; 510/226, 300
See application file for complete search history.

(56) References Cited

U.S. PATENT DOCUMENTS

| 5,500,364 A | 3/1996 | Christensen et al. |
| 5,855,625 A * | 1/1999 | Maurer et al. ............... 8/137 |
| 6,017,871 A | 1/2000 | Baeck et al. |
| 6,902,922 B1 * | 6/2005 | Ness et al. ............... 435/219 |

FOREIGN PATENT DOCUMENTS

| WO | WO 98/20115 | 5/1998 |
| WO | WO 99/27082 | 6/1999 |
| WO | WO 01/44452 | 6/2001 |

* cited by examiner

Primary Examiner—Kathleen Kerr
Assistant Examiner—William W. Moore
(74) Attorney, Agent, or Firm—Elias J. Lambiris

(57) ABSTRACT

The present invention relates to subtilases having a reduced tendency towards inhibition by substances present in eggs, such as the trypsin inhibitor type IV-0. These subtilases are useful exhibiting excellent or improved wash performance on egg stains when used in e.g. cleaning or detergent compositions, such as laundry detergent compositions and dishwash compositions, including automatic dishwash compositions.

29 Claims, 1 Drawing Sheet

```
No:   1        10        20        30        40        50
a)    AQSVPYGVSQIKAPALHSQGYTGSNVKVAVIDSGIDSSHPDLKVAGGASM
b)    AQSVPWGISRVQAPAAHNRGLTGSGVKVAVLDTGI*STHPDLNIRGGASF

No:           60        70        80        90       100
a)    VPSETNPFQDNNSHGTHVAGTVAALNNSIGVLGVAPSASLYAVKVLGADG
b)    VPGEPST*QDGNGHGTHVAGTVAALNNSIGVIGVAPSADLYAVKVLGANG

No:          110       120       130       140       150
a)    SGQYSWIINGIEWAIANNMDVINMSLGGPSGSAALKAAVDKAVASGVVVV
b)    RGSVSGIAQGLEWAAANNMHIANMSLGSDAPSTTLERAVNYATSQGVLVI

No:          160       170       180       190       200
a)    AAAGNEGTSGSSSTVGYPGKYPSVIAVGAVDSSNQRASFSSVGPELDVMA
b)    AATGNNG*SGS***VGYPARYANAMAVGATDQNNRRANFSQYGTGIDIVA

No:          210       220       230       240       250
a)    PGVSIQSTLPGNKYGAYNGTSMASPHVAGAAALILSKHPNWTNTQVRSSL
b)    PGVDIESTYPGSSYDSLSGTSMATPHVAGVAALVKQKNPSWSNVQIRNHL

No:          260       270 275
a)    ENTTTKLGDSFYYGKGLINVQAAAQ
b)    KNTATSLGSTNLYGSGLVNAEAATR
```

```
No:  1         10         20         30         40         50
a)   AQSVPYGVSQIKAPALHSQGYTGSNVKVAVIDSGIDSSHPDLKVAGGASM
b)   AQSVPWGISRVQAPAAHNRGLTGSGVKVAVLDTGI*STHPDLNIRGGASF

No:            60         70         80         90        100
a)   VPSETNPFQDNNSHGTHVAGTVAALNNSIGVLGVAPSASLYAVKVLGADG
b)   VPGEPST*QDGNGHGTHVAGTVAALNNSIGVIGVAPSADLYAVKVLGANG

No:           110        120        130        140        150
a)   SGQYSWIINGIEWAIANNMDVINMSLGGPSGSAALKAAVDKAVASGVVVV
b)   RGSVSGIAQGLEWAAANNMHIANMSLGSDAPSTTLERAVNYATSQGVLVI

No:           160        170        180        190        200
a)   AAAGNEGTSGSSSTVGYPGKYPSVIAVGAVDSSNQRASFSSVGPELDVMA
b)   AATGNNG*SGS***VGYPARYANAMAVGATDQNNRRANFSQYGTGIDIVA

No:           210        220        230        240        250
a)   PGVSIQSTLPGNKYGAYNGTSMASPHVAGAAALILSKHPNWTNTQVRSSL
b)   PGVDIESTYPGSSYDSLSGTSMATPHVAGVAALVKQKNPSWSNVQIRNHL

No:           260        270 275
a)   ENTTTKLGDSFYYGKGLINVQAAAQ
b)   KNTATSLGSTNLYGSGLVNAEAATR
```

Figure 1

SUBTILASE ENZYMES

CROSS-REFERENCE TO RELATED APPLICATIONS

This application claims, under 35 U.S.C. 119, priority or the benefit of Danish application no. PA 2000 01232 filed on Aug. 21, 2000, and U.S. provisional application No. 60/235,459 filed Sep. 26, 2000, the contents of which are fully incorporated herein by reference.

TECHNICAL FIELD

The present invention relates to subtilases having a reduced tendency towards inhibition by substances present in eggs, such as the trypsin inhibitor type IV-0. These subtilases are useful exhibiting excellent or improved wash performance on egg stains when used in e.g. cleaning or detergent compositions, such as laundry detergent compositions and dishwash compositions, including automatic dishwash compositions. The present invention also relates to isolated nucleic acid sequences encoding the subtilases, nucleic acid constructs, recombinant expression vectors, host cells comprising the nucleic acid construct, and methods for producing and using the subtilases of the invention. Further, the present invention relates to cleaning and detergent compositions comprising the subtilase enzymes of the invention as well as to use of such enzymes in detergent compositions and for removal of egg stains.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially most important enzymes are proteases.

An increasing number of commercially used proteases are protein engineered variants of naturally occurring wild type proteases, e.g. DURAZYM® (Novozymes A/S), RELASE® (Novozymes A/S), MAXAPEM® (Gist-Brocades N.V.), PURAFECT® (Genencor International, Inc.).

However, even though a number of useful proteases and protease variants have been described, there is still a need for new improved proteases or protease variants for a number of industrial uses.

In particular, the problem of removing egg stains from e.g. laundry or hard surfaces has been pronounced due to the fact that substances present in the egg white inhibit many serine proteases. Examples of such substances include trypsin inhibitor type IV-0 (Ovo-inhibitor) and trypsin inhibitor type III-0 (Ovomucoid).

Therefore, an object of the present invention, is to provide improved subtilase enzymes, which are not, or which are only to a limited extent, inhibited by such substances. A further object of the present invention is to provide improved subtilase enzymes that are suitable for removal of egg stains from, for example, laundry and/or hard surfaces.

SUMMARY OF THE INVENTION

Thus, in a first aspect the present invention relates to a subtilase enzyme selected from the group consisting of
(a) a subtilase having an amino acid sequence which has at least 95% identity with the amino acid sequence of amino acids 1 to 269 of SEQ ID NO:2; and (b) a subtilase which is encoded by a nucleic acid sequence which hybridizes under low stringency conditions with
    (i) a complementary strand of the nucleic acid sequence of nucleotides 334 to 1140 of SEQ ID NO:1, or
    (ii) a subsequence of (i) of at least 100 nucleotides.

In a second aspect the present invention relates to an isolated nucleic acid sequence comprising a nucleic acid sequence that encodes for the subtilases of the invention.

In a third aspect the present invention relates to an isolated nucleic acid sequence encoding a subtilase, selected from the group consisting of
(a) a nucleic acid sequence having at least 85% identity with the nucleic acid sequence of nucleotides 334 to 1140 of SEQ ID NO:1; and
(b) a nucleic acid sequence which hybridizes under low stringency conditions with
    (i) a complementary strand of the nucleic acid sequence of nucleotides 334 to 1140 of SEQ ID NO:1, or
    (ii) a subsequence of (i) of at least 100 nucleotides.

In a fourth aspect the present invention relates to a nucleic acid construct comprising the nucleic acid sequence according to the invention operably linked to one or more control sequences capable of directing the expression of the subtilase in a suitable host.

In a fifth aspect the present invention relates to a recombinant expression vector comprising the nucleic acid construct according to the invention, a promoter, and transcriptional and translational stop signals.

In a sixth aspect the present invention relates to a recombinant host cell comprising the nucleic acid construct of the invention.

In a seventh aspect the present invention relates to a method for producing the subtilase according to the invention, the method comprising:
(a) cultivating a recombinant host cell according to the invention under conditions conducive to the production of the subtilase; and
(b) recovering the subtilase.

In an eight aspect the present invention relates to a method for producing the subtilase according to the invention, the method comprising:
(a) cultivating a strain from the genus *Bacillus*, preferably from the species *Bacillus clausii*, such as *Bacillus clausii* DSM 13585, to produce a supernatant comprising the subtilase; and
(b) recovering the subtilase.

In a ninth aspect the present invention relates to a cleaning or detergent composition, preferably a laundry or dishwash composition, comprising the subtilase according to the invention.

Further aspects of the present invention relate to use of the subtilases according to the invention in a cleaning or detergent composition; use of the subtilases or the compositions according to the invention for removal of egg stains; a method for cleaning or washing, including a method for removal of egg stains from, a hard surface or laundry comprising contacting the hard surface or the laundry with the composition of the invention.

Concerning alignment and numbering, reference is made to FIG. 1 which shows an alignment between subtilisin BPN' (a) (BASBPN) and a subtilase of the invention (b).

This alignment is in this patent application used as a reference for numbering the residues.

DEFINITIONS

Prior to discussing this invention in further detail, the following terms and conventions will first be defined.

NOMENCLATURE OF AMINO ACIDS

| | | |
|---|---|---|
| A = | Ala = | Alanine |
| V = | Val = | Valine |
| L = | Leu = | Leucine |
| I = | Ile = | Isoleucine |
| P = | Pro = | Proline |
| F = | Phe = | Phenylalanine |
| W = | Trp = | Tryptophan |
| M = | Met = | Methionine |
| G = | Gly = | Glycine |
| S = | Ser = | Serine |
| T = | Thr = | Threonine |
| C = | Cys = | Cysteine |
| Y = | Tyr = | Tyrosine |
| N = | Asn = | Asparagine |
| Q = | Gln = | Glutamine |
| D = | Asp = | Aspartic Acid |
| E = | Glu = | Glutamic Acid |
| K = | Lys = | Lysine |
| R = | Arg = | Arginine |
| H = | His = | Histidine |
| X = | Xaa = | Any amino acid |

NOMENCLATURE OF NUCLEIC ACIDS

| | |
|---|---|
| A = | Adenine |
| G = | Guanine |
| C = | Cytosine |
| T = | Thymine (only in DNA) |
| U = | Uracil (only in RNA) |

NOMENCLATURE AND CONVENTIONS FOR DESIGNATION OF VARIANTS

In describing the various subtilase enzyme variants produced or contemplated according to the invention, the following nomenclatures and conventions have been adapted for ease of reference:

A frame of reference is first defined by aligning the isolated or parent enzyme with subtilisin BPN' (BASBPN).

The alignment can be obtained by the GAP routine of the GCG package version 9.1 to number the subtilases using the following parameters: gap creation penalty=8 and gap extension penalty=8 and all other parameters kept at their default values.

Another method is to use known recognized alignments between subtilases, such as the alignment indicated in WO 91/00345. In most cases the differences will not be of any importance.

Such an alignment between subtilisin BPN' (BASBPN) and a subtilase of the invention is indicated in FIG. 1.

Thereby a number of deletions and insertions will be defined in relation to BASBPN. In FIG. 1, a subtilase according to the invention has 6 deletions in positions 36, 58, 159, 162, 163 and 164 in comparison to BASBPN. These deletions are in FIG. 1 indicated by asterixes (*).

The various modifications performed in a parent enzyme is indicated in general using three elements as follows:

Original Amino Acid Position Substituted Amino Acid

The notation G195E thus means a substitution of a glycine in position 195 with a glutamic acid.

In the case where the original amino acid residue may be any amino acid residue, a short hand notation may at times be used indicating only the position and substituted amino acid:

Position Substituted Amino Acid

Such a notation is particular relevant in connection with modification(s) in homologous subtilases (vide infra).

Similarly when the identity of the substituting amino acid residue(s) is immaterial:

Original Amino Acid Position

When both the original amino acid(s) and substituted amino acid(s) may comprise any amino acid, then only the position is indicated, e.g.: 170.

When the original amino acid(s) and/or substituted amino acid(s) may comprise more than one, but not all amino acid(s), then the selected amino acids are indicated inside brackets:

Original Amino Acid Position {Substituted Amino Acid 1, . . . , Substituted Amino Acidn}

For specific variants the specific three or one letter codes are used, including the codes Xaa and X to indicate any amino acid residue.

Substitutions:

The substitution of Glutamic acid for glycine in position 195 is designated as:

Gly195Glu or G195E or the substitution of any amino acid residue acid for glycine in position 195 is designated as:

Gly195Xaa or G195X or

Gly195 or G195

The substitution of serine for any amino acid residue in position 170 would thus be designated Xaa170Ser or X170S.

or

170Ser or 170S

Such a notation is particular relevant in connection with modification(s) in homologous subtilases (vide infra). 170Ser is thus meant to comprise e.g. both a Lys170Ser modification in BASBPN and Arg170Ser modification in the subtilase according to the invention (cf. FIG. 1).

For a modification where the original amino acid(s) and/or substituted amino acid(s) may comprise more than one, but not all amino acid(s), the substitution of glycine, alanine, serine or threonine for arginine in position 170 would be indicated by Arg170{Gly,Ala,Ser,Thr} or R170{G,A,S,T} to indicate the variants

R170G, R170A, R170S, and R170T.

Deletions:

A deletion of glycine in position 195 will be indicated by:

Gly195* or G195*

Correspondingly, the deletion of more than one amino acid residue, such as the deletion of glycine and leucine in positions 195 and 196 will be designated Gly195*+Leu196* or G195*+L196*

Insertions:

The insertion of an additional amino acid residue such as e.g. a lysine after G195 is indicated by:
Gly195GlyLys or G195GK;

or, when more than one amino acid residue is inserted, such as e.g. a Lys and Ala after G195 this will be indicated as:
Gly195GlyLysAla or G195GKA In such cases the inserted amino acid residue(s) are numbered by the addition of lower case letters to the position number of the amino acid residue preceding the inserted amino acid residue(s). In the above example the sequences 194 to 196 would thus be:

```
              194  195            196
BLSAVI        A  - G    -         L 194  195  195a 195b 196
Variant       A  - G  - K  - A  - L      (SEQ ID NO:3)
```

In cases where an amino acid residue identical to the existing amino acid residue is inserted it is clear that a degeneracy in the nomenclature arises. If for example a glycine is inserted after the glycine in the above example this would be indicated by G195GG. The same actual change could just as well be indicated as A194AG for the change from

```
              194  195       196
BLSAVI        A  - G    -    L
to
              194  195  195a 196
Variant       A  - G  - G  - L      (SEQ ID NO:4)

194 194a 195  196
```

Such instances will be apparent to the skilled person, and the indication G195GG and corresponding indications for this type of insertions are thus meant to comprise such equivalent degenerate indications.

Filling a Gap:

Where a deletion in an enzyme exists in the reference comparison with the subtilisin BPN' sequence used for the numbering, an insertion in such a position is indicated as:
*36Asp or *36D for the insertion of an aspartic acid in position 36.

Multiple Modifications:

Variants comprising multiple modifications are separated by pluses, e.g.:
Arg170Tyr+Gly195Glu or R170Y+G195E representing modifications in positions 170 and 195 substituting tyrosine and glutamic acid for arginine and glycine, respectively.

Thus, Tyr167{Gly,Ala,Ser,Thr}+Arg170{Gly,Ala,Ser,Thr} designates the following variants:

Tyr167Gly + Arg170Gly, Tyr167Gly + Arg170Ala,
Tyr167Gly + Arg170Ser, Tyr167Gly + Arg170Thr,
Tyr167Ala + Arg170Gly, Tyr167Ala + Arg170Ala,

Tyr167Ala + Arg170Ser, Tyr167Ala + Arg170Thr,
Tyr167Ser + Arg170Gly, Tyr167Ser + Arg170Ala,
Tyr167Ser + Arg170Ser, Tyr167Ser + Arg170Thr,
Tyr167Thr + Arg170Gly, Tyr167Thr + Arg170Ala,
Tyr167Thr + Arg170Ser, and Tyr167Thr + Arg170Thr.

This nomenclature is particular relevant relating to modifications aimed at substituting, replacing, inserting or deleting amino acid residues having specific common properties, such as residues of positive charge (K, R, H), negative charge (D, E), or conservative amino acid by; modification(s) of e.g. Tyr167{Gly,Ala,Ser,Thr}+Arg170{Gly,Ala,Ser,Thr}, which signifies substituting a small amino acid for another small amino acid. See section "Detailed description of the invention" for further details.

Proteases

Enzymes cleaving the amide linkages in protein substrates are classified as proteases, or (interchangeably) peptidases (see Walsh, 1979, *Enzymatic Reaction Mechanisms*. W.H. Freeman and Company, San Francisco, Chapter 3).

Numbering of Amino Acid Positions/Residues

If nothing else is mentioned the amino acid numbering used herein correspond to that of the subtilase BPN' (BASBPN) sequence. For further description of the BPN' sequence, see FIG. 1 or Siezen et al., *Protein Engng.* 4 (1991) 719–737.

Serine Proteases

A serine protease is an enzyme which catalyzes the hydrolysis of peptide bonds, and in which there is an essential serine residue at the active site (White, Handler and Smith, 1973 *"Principles of Biochemistry,"* Fifth Edition, McGraw-Hill Book Company, NY, pp. 271–272).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) *Bacteriological Rev.* 41 711–753).

Subtilases

A sub-group of the serine proteases tentatively designated subtilases has been proposed by Siezen et al., *Protein Engng.* 4 (1991) 719–737 and Siezen et al. *Protein Science* 6 (1997) 501–523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences . reference is made to Siezen et al. (1997).

One subgroup of the subtilases, I-S1 or "true" subtilisins, comprises the "classical" subtilisins, such as subtilisin 168 (BSS168), subtilisin BPN', subtilisin Carlsberg (ALCALASE®, Novozymes A/S), and subtilisin DY (BSSDY).

A further subgroup of the subtilases, I-S2 or high alkaline subtilisins, is recognized by id* Siezen et al. (supra). Subgroup I-S2 proteases are described as highly alkaline subtilisins and comprises enzymes such as subtilisin PB92 (BAALKP) (MAXACAL®, Gist-Brocades NV), subtilisin 309 (BLSAVI, BLS309)(SAVINASE®, Novozymes A/S), subtilisin 147 (BLS147) (ESPERASE®, Novozymes A/S), and alkaline elastase YaB (BSEYAB).

Parent Subtilase

The term "parent subtilase" describes a subtilase defined according to Siezen et al. (1991 and 1997). For further details see description of "SUBTILASES" immediately above. A parent subtilase may also be a subtilase isolated from a natural source, wherein subsequent modifications have been made while retaining the characteristic of a subtilase. Furthermore, a parent subtilase may also be a subtilase which has been prepared by the DNA shuffling technique, such as described by J. E. Ness et a., Nature Biotechnology, 17, 893–896 (1999).

Alternatively the term "parent subtilase" may be termed "wild type subtilase".

Modification(s) of a Subtilase

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase Variant

In the context of this invention, the term subtilase variant or mutated subtilase means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilase protease is produced when expressed in a suitable host. Analogously, the mutant gene may also be derived from a parent gene produced by DNA shuffling technique.

Homologous Subtilase Sequences

In the present context the homology between two amino acid sequences is described by the parameter "identity".

In order to determine the degree of identity between two subtilases the GAP routine of the GCG package version 9.1 can be applied (infra) using the same settings. The output from the routine is besides the amino acid alignment the calculation of the "Percent Identity" between the two sequences.

Based on this description it is routine for a person skilled in the art to identify suitable homologous subtilases and corresponding homologous active site loop regions, which can be modified according to the invention.

Isolated Nucleic Acid Sequence

The term "isolated nucleic acid sequence" as used herein refers to a nucleic acid sequence, which has been isolated and purified and is thus in a form suitable for use within genetically engineered protein production systems. Such isolated molecules may be those that are separated from their natural environment and include cDNA and genomic clones as well as nucleic acid sequences derived from DNA shuffling experiments or from site-directed mutagenisis experiments. Isolated nucleic acid sequences of the present invention are free of other genes with which they are ordinarily associated, but may include 5' and 3' untranslated regions such as promoters and terminators. The identification of associated regions will be evident to one of ordinary skill in the art (see for example, Dynan and Tijan, Nature 316:774–78, 1985). The term "isolated nucleic acid sequence" may alternatively be termed "isolated DNA sequence", "cloned nucleic acid sequence" or "cloned DNA sequence".

Isolated Protein

When applied to a protein, the term "isolated" indicates that the protein has been removed from its native environment.

In a preferred form, the isolated protein is substantially free of other proteins, particularly other homologous proteins (i.e. "homologous impurities" (see below)).

An isolated protein is more than 10% pure, preferably more than 20% pure, more preferably more than 30% pure, as determined by SDS-PAGE. Further it is preferred to provide the protein in a highly purified form, i.e., more than 40% pure, more than 60% pure, more than 80% pure, more preferably more than 95% pure, and most preferably more than 99% pure, as determined by SDS-PAGE.

The term "isolated protein" may alternatively be termed "purified protein".

Homologous Impurities

The term "homologous impurities" means any impurity (e.g. another polypeptide than the subtilase of the invention), which originate from the homologous cell where the subtilase of the invention is originally obtained from.

Obtained From

The term "obtained from" as used herein in connection with a specific microbial source, means that the polynucleotide and/or subtilase produced by the specific source, or by a cell in which a gene from the source has been inserted.

Substrate

The term "substrate" used in connection with a substrate for a protease should be interpreted in its broadest form as comprising a compound containing at least one peptide bond susceptible to hydrolysis by a subtilisin protease.

Product

The term "product" used in connection with a product derived from a protease enzymatic reaction should, in the context of the present invention, be interpreted to include the products of a hydrolysis reaction involving a subtilase protease. A product may be the substrate in a subsequent hydrolysis reaction.

Wash Performance

In the present context the term "wash performance" is used as an enzyme's ability to remove egg stains present on the object to the cleaned during e.g. wash or hard surface cleaning. See also the "Model Detergent Wash Performance Test" in Example 2, herein.

Performance Factor

The term "Performance Factor" is defined with respect to the below formula $$P = R_{subtilase} - R_{savinase}$$

wherein P is the Performance Factor, $R_{subtilase}$ is the reflectance of the test material after being treated with a subtilase enzyme of the invention as described in the "Model Detergent Wash Performance Test", and $R_{savinase}$ is the reflectance of the test material after being treated with Savinase® as described in the "Model Detergent Wash Performance Test". For further details, see the "Model Detergent Wash Performance Test" in Example 2, herein.

Residual Activity

The term "Residual Activity" is defined as described in the "Ovo-inhibition Assay" herein (see Example 3).

BRIEF DESCRIPTION OF THE DRAWING

FIG. 1 shows an alignment between subtilisin BPN' (a) (SEQ ID NO:9) and the amino acid sequence of a subtilase of the invention (b) (SEQ ID NO:2) using the GAP routine mentioned above.

DETAILED DESCRIPTION OF THE INVENTION

In a first interesting aspect of the present invention, the subtilase enzyme is an isolated subtilase which has at least 95% identity with the amino acid sequence of amino acids 1 to 269 of SEQ ID NO:2 (i.e. the mature subtilase). In an interesting embodiment of the invention the subtilase has at least 96%, preferably at least 97%, more preferably at least 98%, in particular at least 99% identity with the amino acid sequence of amino acids 1 to 269 of SEQ ID NO:2 (hereinafter "homologous subtilases"). In another interesting embodiment of the invention the isolated subtilase comprises or consists of the amino acid sequence of amino acids 1 to 269 of SEQ ID NO:2.

Alignments of sequences and calculation of identity scores can be done using the GAP routine (and the same settings) mentioned previously.

By performing such alignments, the following identities (in percentage) between the amino acid sequences of the subtilase having the amino acid sequence of SEQ ID NO:2 and various known subtilases were found:

|  | BLSAVI | BLAP | BASBPN | BLSCAR | SEQ ID NO: 2 |
|---|---|---|---|---|---|
| BLSAVI | 100 |  |  |  |  |
| BLAP[1)] | 98 | 100 |  |  |  |
| BASBPN | 58 | 58 | 100 |  |  |
| BLSCAR | 60 | 60 | 68 | 100 |  |
| SEQ ID NO: 2 | 93 | 94 | 57 | 58 | 100 |

[1)]BLAP (*Bacillus lentus* Alkaline Protease) has been described in U.S. Pat. No. 5,352,604

In another interesting embodiment of the invention the isolated subtilase is encoded by a nucleic acid sequence which hybridizes under low stringency conditions, preferably under medium stringency conditions, more preferably under high stringency conditions with (i) a complementary strand of the nucleic acid sequence of nucleotides 334 to 1140 of SEQ ID NO:1, or (ii) a subsequence of (i) of at least 100 nucleotides (J. Sambrook, E. F. Fritsch, and T. Maniatis, 1989, *Molecular Cloning, A Laboratory Manual*, 2d edition, Cold Spring Harbor, N.Y.).

The subsequence of the complementary strand of the nucleic acid sequence of nucleotides 334 to 1140 of SEQ ID NO:1 may be at least 100 nucleotides or preferably at least 200 nucleotides. Moreover, the subsequence should encode a subtilase fragment, which has proteolytic activity. The subtilases may also be allelic variants or fragments of the subtilases that have proteolytic activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding subtilases having proteolytic activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA, which hybridizes with the probes described above and which encodes a subtilase according to the invention. Genomic or other DNA from such other organisms may be separated by agarose or polyacrylamide gel electrophoresis, or other separation techniques known by the skilled person. DNA from the libraries or the separated DNA may be transferred to and immobilized on nitrocellulose or other suitable carrier materials. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under low to high stringency conditions. Molecules to which the nucleic acid probe hybridizes under these conditions are detected using X-ray film.

For long probes of at least 100 nucleotides in length, low to high stringency conditions are defined as prehybridization and hybridization at 42° C. in 5×SSPE, 0.3% SDS, 200 µg/ml sheared and denatured salmon sperm DNA, and either 25% formamide for low stringency, 35% formamide for medium stringency, or 50% formamide for high stringency, following standard Southern blotting procedures.

For long probes of at least 100 nucleotides in length, the carrier material is finally washed three times each for 15 minutes using 2×SSC, 0.2% SDS preferably at least at 50° C. (low stringency), more preferably at least at 55° C. (medium stringency), even more preferably at least at 65° C. (high stringency).

For short probes, which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml, following standard Southern blotting procedures.

For short probes, which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

It is well known in the art that a so-called conservative substitution of one amino acid residue to a similar amino acid residue is expected to produce only a minor change in the characteristic of the enzyme.

Table I below list groups of conservative amino acid substitutions.

TABLE I

Conservative amino acid substitutions

| Common Property | Amino Acid |
|---|---|
| Basic (positive charge) | K = lysine |
| | H = histidine |
| Acidic (negative charge) | E = glutamic acid |
| | D = aspartic acid |
| Polar | Q = glutamine |
| | N = asparagines |
| Hydrophobic | L = leucine |
| | I = isoleucine |
| | V = valine |
| | M = methionines |
| Aromatic | F = phenylalanine |
| | W = tryptophan |
| | Y = tyrosine |
| Small | G = glycine |
| | A = alanine |
| | S = serine |
| | T = threonine |

Therefore, in a further interesting embodiment of the invention, a subtilase having the amino acid sequence of SEQ ID NO:2 is modified by the substitution, deletion and/or insertion of one or more amino acid residues.

Therefore, in a further interesting embodiment of the invention, the subtilase is a variant of the subtilase having the amino acid sequence of amino acids 1 to 269 of SEQ ID NO:2, said variant comprises at least one modification, i.e. substitution, deletion and/or insertion, as compared to the amino acid sequence of amino acids 1 to 269 of SEQ ID NO:2. Preferably, the number of modifications is at the most 18, such as at the most 17, e.g. at the most 16 or at the most 15. In a more preferred embodiment the number of modifications is at the most 14, e.g. at the most 13, at the most 12, at the most 11, at the most 10, at the most 9, at the most 8, at the most 7, at the most 6, or at the most 5. In particular interesting embodiments of the invention, the number of modifications is at the most 4, preferably at the most 3, e.g. at the most 2.

A modified subtilase of the invention has preferably an identity to the amino acid sequence of SEQ ID. NO:2 of 95% or more.

Especially, combinations with other modifications known in the art to provide improved properties to the enzyme are envisaged. The art describes a number of subtilase variants with different improved properties and a number of those are mentioned in the "Background of the invention" section herein (vide supra).

Thus, modification of the amino acid sequence SEQ ID NO:2 in one or more of the following positions are contemplated as being of particular relevance (in BASBPN numbering): 27, 36, 56, 76, 87, 96, 97, 98, 99, 100, 101, 103, 104, 120, 123, 129, 131, 132, 133, 143, 159, 167, 170, 192, 194, 206, 217, 218, 222, 224, 232, 235, 236, 245, 248, 252 and 274.

In particular, the following variants of the subtilase of the invention are considered appropriate for combination (in BASBPN numbering): K27R, *36D, T56P, N76D, N87S, A97N, A98AT, A98AS, N99ND, N99NR, N99A, N99T, R101G, P103A, V104A, V104I, V104N, V104Y, D120H, N123S, P129K, P131H, A133P, A133D, A133E, T143K, *159D, *159E, Y167X, Y167A, R170X, R170S, A194P, Q206E, F217R, N218S, M222S, M222A, T224S, A232V, K235L, Q236H, 0245R, N248D, N252K and T274A.

Of further particular interest are variants of the subtilase of the invention, wherein the modifications comprise any of the modifications V104N+R101G, K27R+V104Y+N123S+T274A, N76D+V104A, or R101G+P103A+V104I+*159D+A232V+Q236H+Q245R+N248D+N252K; or other combinations of these modifications (K27R, N76D, R101G, P103A, V104I, V104N, V104A, V104Y, N123S, *159D, A232V, Q236H, Q245R, N248D, N252K T274A), in combination with any one or more of the modifications indicated above or below.

Furthermore, it is contemplated that insertion of at least one additional amino acid residue in the active site (b) loop region, corresponding to insertion of at least one additional amino acid residue from position 95 to position 103 (BASBPN numbering), will confer additional wash performance to the subtilase of the invention. In particular, it is preferred to insert at least one additional amino acid residue, such as one additional amino acid residue, in the following positions: between positions 98 and 99 (BASBPN numbering), and between positions 99 and 100 (BASBPN numbering).

As mentioned above, the subtilases of the invention are only inhibited by trypsin inhibitor type IV-0 to a limited extent and, consequently, they exhibit excellent wash performance on egg stains. Therefore, in order to enable the skilled person—at an early stage of his development work—to select effective and preferred subtilases for this purpose, the present inventors have provided a suitable preliminary test, which can easily be carried out by the skilled person in order to initially assess the performance of the subtilase in question.

Thus, the "Ovo-inhibition Assay" disclosed in Example 3 herein may be employed to initially assess the potential of a selected subtilase. In other words, the "Ovo-inhibition Assay" may be employed to assess whether a selected enzyme will be inhibited, and to what extent, by the trypsin inhibitor type IV-0. Using this test, the suitability of a selected subtilase to remove egg stains can be assessed, the rationale being that if a selected subtilase is strongly inhibited by trypsin inhibitor type IV-0, it is normally not necessary to carry out further test experiments.

Therefore, a subtilase which is particular interesting for the purposes described herein, is a subtilase which—when tested in the "Ovo-inhibition Assay" described in Example 3 herein—has a Residual Activity of at least 15%, such as at least 20%, preferably at least 25%, such as at least 30%, more preferably at least 35%.

Evidently, it is preferred that the subtilase of the invention fulfils the above criteria on at least the stated lowest level, more preferably at the stated intermediate level and most preferably on the stated highest level.

Alternatively, or in addition to the above-mentioned assay, the suitability of a selected subtilase may be tested in the "Model Detergent Wash Performance Test" disclosed in Example 2 herein. The "Model Detergent Wash Perfomance Test" may be employed to assess the ability of a subtilase, when incorporated in a standard detergent composition, to remove egg stains from a standard textile as compared to a reference system, in this case Savinase® (incorporated in the same model detergent system and tested under identical conditions). Using this test, the suitability of a selected subtilase to remove egg stains can be initially investigated, the rationale being that if a selected subtilase does not show a significant improvement in the test compared to Savinase®, it is normally not necessary to carry out further test experiments.

Therefore, subtilases which are particular interesting for the purposes described herein, are such subtilases which, when tested in a model detergent composition comprising

| | |
|---|---|
| 6.2% | LAS (Nansa 80S) |
| 2% | Sodium salt of $C_{16}$–$C_{18}$ fatty acid |
| 4% | Non-ionic surfactant (Plurafax LF404) |
| 22% | Zeolite P |
| 10.5% | $Na_2CO_3$ |
| 4% | $Na_2Si_2O_5$ |
| 2% | Carboxymethylcellulose (CMC) |
| 6.8% | Acrylate liquid CP5 40% |
| 20% | Sodium perborate (empirical formula $NaBO_2.H_2O_2$) |
| 0.2% | EDTA |
| 21% | $Na_2SO_4$ |
| Water | (balance) | as described in the "Model Detergent Wash Performance Test" herein, shows an improved wash performance on egg stains as compared to Savinase® tested under identical conditions.

The improvement in the wash performance may be quantified by employing the so-called "Performance Factor" defined in Example 2, herein.

In a very interesting embodiment of the invention, the subtilase of the invention, when tested in the "Wash Performance Test" has a Performance Factor of at least 1, such as at least 1.5, e.g. at least 2, preferably at least 2.5, such as at least 3, e.g. at least 3.5, in particular at least 4, such as at least 4.5, e.g. at least 5.

Evidently, it is preferred that the subtilase of the invention fulfils the above criteria on at least the stated lowest level, more preferably at the stated intermediate level and most preferably on the stated highest level.

The subtilase of the invention may be isolated from a natural source, i.e. the subtilase of the invention may, for example, be a bacterial subtilase, e.g. a gram positive bacterial subtilase such as a *Bacillus* polypeptide, e.g., a *Bacillus clausli* (formerly *Bacillus lentus*), a *Bacillus alkalophilus, Bacillus amyloliquefaciens, Bacillus brevis, Bacillus circulans, Bacillus coagulans, Bacillus lautus, Bacillus licheniformis, Bacillus megaterium, Bacillus stearothermophilus, Bacillus subtilis,* or *Bacillus thuringiensis* subtilase; or a *Streptomyces* subtilase, e.g., a *Streptomyces lividans* or *Streptomyces murinus* subtilase; or a gram negative bacterial subtilase, e.g., an *E. coli* or a *Pseudomonas* sp. subtilase.

The subtilase of the present invention may also be a fungal polypeptide, and more preferably a yeast subtilase such as a *Candida, Kluyveromyces, Pichia, Saccharomyces, Schizosaccharomyces,* or *Yarrowia* subtilase; or more preferably a filamentous fungal subtilase such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* or *Trichoderma* subtilase.

In an interesting embodiment, the subtilase is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* subtilase.

In another interesting embodiment, the subtilase is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* subtilase.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammiung von Mikroorganismen und Zellkulturen GmbH (DSM), Centraalbureau Voor Schimmelcultures (CBS), and Agricultural Research Service Patent Culture Collection, Northern Regional Research Center (NRRL).

A particular suitable *Bacillus* strain from which the subtilase of the invention may be isolated is the strain *Bacillus clausii* HSB10 (also denoted alkaline *Bacillus* strain HS433) which was deposited according to the Budapest Treaty on the International Recognition of the Deposits of Microorganisms for the Purpose of Patent Procedures on 5 Jul. 2000 at the Deutsche Sammiung von Mikroorganismen und Zellkulturen GmbH, Mascheroder Weg 1 B, D-38124 Braunschweig, Germany, and designated accession No. DSM 13585. The deposit was made by Novo Nordisk A/S and has been assigned to Novozymes A/S.

Furthermore, such subtilases may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a subtilase has been detected with the probe(s), the sequence may be isolated or cloned by utilizing techniques which are known to those of ordinary skill in the art (see, e.g., Sambrook et al., 1989, supra).

Moreover, the subtilase of the invention may be constructed by standard techniques for artificial creation of diversity, such as by DNA shuffling of different subtilase genes (see WO 95/22625 and J. E. Ness et al., Nature Biotechnology, 17, 893–896 (1999)).

Many methods for cloning a subtilase of the invention and for introducing insertions into genes (e.g. subtilase genes) are well known in the art, cf. the references cited in the "BACKGROUND OF THE INVENTION" section.

In general standard procedures for cloning of genes and introducing insertions (random and/or site directed) into said genes may be used in order to obtain a subtilase enzyme of the invention. For further description of suitable techniques reference is made to Examples herein (vide infra) and (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990); and WO 96/34946.

Further, a subtilase enzyme of the invention may be constructed by standard techniques for artificial creation of diversity, such as by DNA shuffling of different subtilase genes (WO 95/22625; Stemmer WPC, Nature 370:389–91 (1994)). It is contemplated that DNA shuffling of e.g. the gene encoding Savinase® with one or more partial subtilase sequences identified in nature will, after subsequent screening for improved wash performance, provide subtilases according to the invention.

Nucleic Acid Sequences

The present invention also relates to an isolated nucleic acid sequence, which encodes a subtilase of the present invention.

In one interesting embodiment, the nucleic acid sequence has at least 85% identity with the nucleic acid sequence of nucleotides 334 to 1140 of SEQ ID NO:1. Preferably, the nucleic acid sequence has at least 86%, such as at least 87%, e.g. at least 88%, more preferably at least 89%, such as at least 90%, e.g. at least 91%, even more preferably at least 92%, such as at least 93%, e.g. at least 94%, most preferably at least 95%, such as at least 96%, e.g. at least 97%, in particular at least 98%, such as at least 99% identity with the nucleic acid sequence of nucleotides 334 to 1140 of SEQ ID NO:1. In another interesting embodiment of the invention the nucleic acid sequence comprises the nucleic acid sequence of nucleotides 334 to 1140 of SEQ ID NO:1, an allelic variant thereof, or a fragment thereof capable of encoding a subtilase according to the invention. Obviously, the nucleic acid sequence may consist of the nucleic acid sequence of nucleotides 334 to 1140 of SEQ ID NO:1.

The present invention also encompasses nucleic acid sequences which encode a polypeptide having the amino acid sequence of SEQ ID NO:2, which differ from SEQ ID NO:2 by virtue of the degeneracy of the genetic code. The present invention also relates to subsequences of SEQ ID NO:1 which encode fragments of SEQ ID NO:2 that have proteolytic activity.

A subsequence of SEQ ID NO:1 is a nucleic acid sequence encompassed by nucleotides 334 to 1140 SEQ ID NO:1 except that one or more nucleotides from the 5' and/or 3' end have been deleted.

The present invention also relates to isolated nucleic acid sequences encoding a subtilase of the present invention, which hybridize under low stringency conditions, preferably under medium stringency conditions, more preferably under high stringency conditions, with (i) a complementary strand of the nucleic acid sequence of nucleotides 334 to 1140 of SEQ ID NO:1, or (ii) a subsequence of (i) of at least 100 nucleotides. The present invention also relates to complementary strands of (i) and (ii).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used.

An isolated nucleic acid sequence can, for example, be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the subtilase, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

For purposes of the present invention, the degree of identity between two nucleic acid sequences is determined as described above.

Modification of a nucleic acid sequence encoding a subtilase of the present invention may be necessary for the synthesis of subtilases substantially similar to the subtilase. The term "substantially similar" to the subtilase refers to non-naturally occurring forms of the subtilase. These subtilases may differ in some engineered way from the subtilase isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the subtilase encoded by the nucleic acid sequence, but which correspond to the codon al usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active subtilase. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for proteolytic activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

Nucleic Acid Constructs

The present invention also relates to nucleic acid constructs comprising a nucleic acid sequence of the present invention operably linked to one or more control sequences capable of directing the expression of the polypeptide in a suitable host cell.

An isolated nucleic acid sequence encoding a subtilase of the present invention may be manipulated in a variety of ways to provide for expression of the subtilase. Manipulation of the nucleic acid sequence prior to its insertion into a vector may be desirable or necessary depending on the expression vector. The techniques for modifying nucleic acid sequences utilizing recombinant DNA methods are well known in the art.

The control sequences include all components, which are necessary or advantageous for the expression of a subtilase of the present invention. Each control sequence may be native or foreign to the nucleic acid sequence encoding the subtilase. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a subtilase.

The control sequence may be an appropriate promoter sequence, a nucleic acid sequence which is recognized by a host cell for expression of the nucleic acid sequence. The promoter sequence contains transcriptional control sequences which mediate the expression of the subtilase. The promoter may be any nucleic acid sequence which shows transcriptional activity in the host cell of choice including mutant, truncated, and hybrid promoters, and may be obtained from genes encoding extracellular or intracellular subtilases either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the subtilase. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a subtilase and directs the encoded subtilase into the cell's secretory pathway. The 5' end of the coding sequence of the nucleic acid sequence may inherently contain a signal peptide coding region naturally linked in translation reading frame with the segment of the coding region which encodes the secreted subtilase. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the subtilase. However, any signal peptide coding region which directs the expressed subtilase into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57:109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a subtilase. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a subtilase, the propeptide region is positioned next to the amino terminus of a subtilase and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to a recombinant expression vector comprising the nucleic acid construct of the invention, a promoter, and transcriptional and translational stop signals.

The recombinant expression vector comprising the nucleic acid construct encoding the enzyme of the invention may be any vector which may conveniently be subjected to recombinant DNA procedures.

The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid.

Alternatively, the vector may be one that on introduction into a host cell is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gen, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cell

The present invention also relates to a recombinant host cell comprising the nucleic acid construct of the invention.

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells including plants.

Examples of bacterial host cells which, on cultivation, are capable of producing the enzyme of the invention are gram-positive bacteria such as strains of Bacillus, such as strains of B. subtilis, B. licheniformis, B. clauslii, B. brevis, B. stearothermophilus, B. alkalophilus, B. amyloliquefaciens, B. coagulans, B. circulans, B. lautus, B. megatherium or B. thuringiensis, in particular B. clausii, or strains of Streptomyces, such as S. lividans or S. murinus, or gram-negative bacteria such as Echerichia coli.

The transformation of the bacteria may be effected by protoplast transformation, electroporation, conjugation, or by using competent cells in a manner known per se (cf. Sambrook et al., supra).

When expressing the enzyme in bacteria such as E. coli, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as Bacillus or Streptomyces strains, the enzyme may be retained in the cytoplasm, or may be directed to the extracellular medium by a bacterial secretion sequence. In the latter case, the enzyme may be recovered from the medium as described below.

Method of Producing a Subtilases of the Invention

The present invention further relates to a method for producing a subtilase of the invention, the method comprising:

a) cultivating a recombinant host cell of the invention under conditions conducive to the production of the subtilase; and b) recovering the subtilase.

When an expression vector comprising a DNA sequence encoding the enzyme is transformed into a heterologous host cell it is possible to enable heterologous recombinant production of the enzyme of the invention.

Thereby it is possible to make a highly purified subtilase composition, characterized in being free from homologous impurities.

In this context homologous impurities means any impurities (e.g. other polypeptides than the enzyme of the invention) which originate from the homologous cell where the enzyme of the invention is originally obtained from.

The medium used to culture the transformed host cells may be any conventional medium suitable for growing the host cells in question. The expressed subtilase may conveniently be secreted into the culture medium and may be recovered therefrom by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

The present invention also relates to methods for producing a subtilase of the present invention, the method comprising (a) cultivating a strain from the genus Bacillus to produce a supernatant comprising the subtilase; and (b) recovering the subtilase.

Preferably, the strain is of the species Bacillus clausii, and more preferably Bacillus clausii DSM 13585.

In the production methods of the present invention, the cells are cultivated in a nutrient medium suitable for production of the subtilase using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the subtilase to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the subtilase is secreted into the nutrient medium, the subtilase can be recovered directly from the medium. If the polypeptide is not secreted, it can be recovered from cell lysates.

The subtilase may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting subtilase may be recovered by methods known in the art. For example, the subtilase may be recovered from the nutrient medium by conventional procedures including, but not limited to, centrifugation, filtration, extraction, spray-drying, evaporation, or precipitation.

The subtilases of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Use of a Subtilase of the Invention

A subtilase enzyme of the invention may be used for a number of industrial applications, in particular within the detergent industry. Thus, the present invention also relates to a cleaning or detergent composition, preferably a laundry or dishwash composition, in particular an automatic dishwash composition, comprising the subtilase enzyme of the invention.

In general, cleaning and detergent compositions are well described in the art and reference is made to WO 96/34946; WO 97/07202; WO 95/30011 for further description of suitable cleaning and detergent compositions.

Furthermore the examples herein demonstrate the improvements in wash performance on egg stains for the subtilases of the invention.

Detergent Compositions

The subtilase of the invention may be added to and thus become a component of a cleaning or detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the subtilase enzyme of the invention. The detergent additive as well as the detergent composition may comprise one or more other enzymes such as another protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98120115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from H. lanuginosa (T. lanuginosus) as described in EP 258 068 and EP 305 216 or from H. insolens as described in WO 96/13580, a Pseudomonas lipase, e.g. from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g. from B. subtilis (Dartois et al. (1993), Biochemica et Biophysica Acta, 1131, 253–360), B. stearothermophilus (JP 64/744992) or B. pumilus (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases: Suitable amylases ($\alpha$ and/or $\beta$) include those of bacterial or fungal origin. Chemically modified or protein engineered mutants are included. Amylases include, for example, $\alpha$-amylases obtained from Bacillus, e.g. a special strain of B. licheniformis, described in more detail in GB 1,296,839.

Examples of useful amylases are the variants described in WO 94102597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having colour care . benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from C. cinereus, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition typically comprises one or more surfactants, which may be non-ionic including semipolar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liquor, preferably 0.05–5 mg of enzyme protein per liter of wash liquor, in particular 0.1–1 mg of enzyme protein per liter of wash liquor.

The enzyme of the invention may additionally be incorporated in the detergent formulations disclosed in WO 97/07202 which is hereby incorporated as reference.

The invention is described in further detail in the following examples which are not in any way intended to limit the scope of the invention as claimed.

In the detergent compositions, the abbreviated component identifications have the following meanings:

| | |
|---|---|
| LAS: | Sodium linear $C_{12}$ alkyl benzene sulphonate |
| TAS: | Sodium tallow alkyl sulphate |
| XYAS: | Sodium $C_{1X}$–$C_{1Y}$ alkyl sulfate |
| SS: | Secondary soap surfactant of formula 2-butyl octanoic acid |
| 25EY: | A $C_{12}$–$C_{15}$ predominantly linear primary alcohol condensed with an average of Y moles of ethylene oxide |
| 45EY: | A $C_{14}$–$C_{15}$ predominantly linear primary alcohol condensed with an average of Y moles of ethylene oxide |
| XYEZS: | $C_{1X}$–$C_{1Y}$ sodium alkyl sulfate condensed with an average of Z moles of ethylene oxide per mole |
| Nonionic: | $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF GmbH |
| CFAA: | $C_{12}$–$C_{14}$ alkyl N-methyl glucamide |
| TFAA: | $C_{16}$–$C_{18}$ alkyl N-methyl glucamide |
| Silicate: | Amorphous Sodium Silicate ($SiO_2$:$Na_2O$ ratio = 2.0) |
| NaSKS-6: | Crystalline layered silicate of formula δ-$Na_2Si_2O_5$ |
| Carbonate: | Anhydrous sodium carbonate |
| Phosphate: | Sodium tripolyphosphate |

-continued

| | |
|---|---|
| MA/AA: | Copolymer of 1:4 maleic/acrylic acid, average molecular weight about 80,000 |
| Polyacrylate: | Polyacrylate homopolymer with an average molecular weight of 8,000 sold under the tradename PA30 by BASF Gmbh |
| Zeolite A: | Hydrated Sodium Aluminosilicate of formula $Na_{12}(AlO_2SiO_2)_{12}.27H_2O$ having a primary particle size in the range from 1 to 10 micrometers |
| Citrate: | Tri-sodium citrate dihydrate |
| Citric: | Citric Acid |
| Perborate: | Anhydrous sodium perborate monohydrate bleach, empirical formula $NaBO_2.H_2O_2$ |
| PB4: | Anhydrous sodium perborate tetrahydrate |
| Percarbonate: | Anhydrous sodium percarbonate bleach of empirical formula $2Na_2CO_3.3H_2O_2$ |
| TAED: | Tetraacetyl ethylene diamine |
| CMC: | Sodium carboxymethyl cellulose |
| DETPMP: | Diethylene triamine penta (methylene phosphonic acid), marketed by Monsanto under the Tradename Dequest 2060 |
| PVP: | Polyvinylpyrrolidone polymer |
| EDDS: | Ethylenediamine-N, N'-disuccinic acid, [S,S] isomer in the form of the sodium salt |
| Suds Suppressor: | 25% paraffin wax Mpt 50° C., 17% hydrophobic silica, 58% paraffin oil |
| Granular Suds suppressor: | 12% Silicone/silica, 18% stearyl alcohol, 70% starch in granular form |
| Sulphate: | Anhydrous sodium sulphate |
| HMWPEO: | High molecular weight polyethylene oxide |
| TAE 25: | Tallow alcohol ethoxylate (25) |

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme | 0.1 |
| PVP | 0.5 |
| TAED | 3.0 |
| Boric acid | 4.0 |
| Perborate | 18.0 |
| Phenol sulphonate | 0.1 |
| Minors | up to 100% |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10.0 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |

-continued

| | | |
|---|---|---|
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | | |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

| Powder automatic dishwash composition I | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetyl ethylene diamine (TAED) | 1–4% |
| Sodium sulphate | 5–33% |
| Enzymes | 0.0001–0.1% |
| Powder automatic dishwash composition II | |
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodium perborate monohydrate | 5–10% |
| Tetraacetyl ethylene diamine (TAED) | 1–2% |
| Polyacrylate polymer (e.g. maleic acid/acrylic acid copolymer) | 6–25% |
| Enzymes | 0.0001–0.1% |
| Perfume | 0.1–0.5% |
| Water | 5–10 |
| Powder automatic dishwash composition III | |
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetyl ethylene diamine (TAED) | 0–6% |
| Maleic acid/acrylic acid copolymer | 0–5% |
| Clay | 1–3% |
| Polyamino acids | 0–20% |
| Sodium polyacrylate | 0–8% |
| Enzymes | 0.0001–0.1% |
| Powder automatic dishwash composition IV | |
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetyl ethylene diamine (TAED) | 0–3% |
| Polymer | 0–4% |
| Maleic acid/acrylic acid copolymer | 0–5% |
| Organic phosphonate | 0–4% |
| Clay | 1–2% |
| Enzymes | 0.0001–0.1% |
| Sodium sulphate | Balance |
| Powder automatic dishwash composition V | |
| Nonionic surfactant | 1–7% |
| Sodium disilicate | 18–30% |
| Trisodium citrate | 10–24% |
| Sodium carbonate | 12–20% |
| Monopersulphate ($2KHSO_5 \cdot KHSO_4 \cdot K_2SO_4$) | 15–21% |
| Bleach stabilizer | 0.1–2% |
| Maleic acid/acrylic acid copolymer | 0–6% |
| Diethylene triamine pentaacetate, pentasodium salt | 0–2.5% |
| Enzymes | 0.0001–0.1% |
| Sodium sulphate, water | Balance |
| Powder and liquid dishwash composition with cleaning surfactant system VI | |
| Nonionic surfactant | 0–1.5% |
| Octadecyl dimethylamine N-oxide dihydrate | 0–5% |
| 80:20 wt. C18/C16 blend of octadecyl dimethylamine N-oxide dihydrate and hexadecyldimethyl amine N-oxide dihydrate | 0–4% |
| 70:30 wt. C18/C16 blend of octadecyl bis (hydroxyethyl)amine N-oxide anhydrous and hexadecyl bis (hydroxyethyl)amine N-oxide anhydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{13}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetyl ethylene diamine (TAED) | 0–4% |
| Maleic acid/acrylic acid copolymer | 0–7.5% |
| Sodium sulphate | 0–12.5% |
| Enzymes | 0.0001–0.1% |

-continued

| Non-aqueous liquid automatic dishwashing composition VII | |
|---|---|
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes | 0.0001–0.1% |
| Non-aqueous liquid dishwashing composition VIII | |
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate polymer | 5.0–15.0% |
| Clay gel thickener (e.g. bentonite) | 0.0–10.0% |
| Hydroxypropyl cellulose polymer | 0.0–0.6% |
| Enzymes | 0.0001–0.1% |
| Liquid carrier selected from higher lycols, polyglycols, polyoxides and glycol ethers | Balance |
| Thixotropic liquid automatic dishwashing composition IX | |
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminium tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decyldiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes | 0.0001–0.1% |
| Suds suppressor, dye, perfumes, water | Balance |
| Liquid automatic dishwashing composition X | |
| Alcohol ethoxylate | 0–20% |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetyl ethylene diamine (TAED) | 0–8% |
| Maleic acid/acrylic acid copolymer | 4–8% |
| Enzymes | 0.0001–0.1% |
| Liquid automatic dishwashing composition containing protected bleach particles XI | |
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes | 0.0001–0.1% |
| Water | Balance |

XII: Automatic dishwashing compositions as described in I, II, III, IV, VI and X, wherein perborate is replaced by percarbonate.

XIII: Automatic dishwashing compositions as described in I–VI, which additionally contain a manganese catalyst. The manganese catalyst may, e.g., be one of the compounds described in "Efficient manganese catalysts for low-temperature bleaching", *Nature,* (1994), 369, 637–639.

Materials and Methods

Proteolytic Activity

In the context of this invention proteolytic activity is expressed in Kilo NOVO Protease Units (KNPU). The activity is determined relatively to an enzyme standard (SAVINASE®), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novozymes AIS, Denmark, which folder is hereby included by reference.

A GU is a Glycine Unit, defined as the proteolytic enzyme activity which, under standard conditions, during a 15 minutes' incubation at 40° C., with N-acetyl casein as substrate, produces an amount of $NH_2$-group equivalent to I mmole of glycine.

Enzyme activity can also be measured using the PNA assay, according to reaction with the soluble substrate succinyl-alanine-alanine-proline-phenyl-alanine-para-nitrophenol, which is described in the Journal of American Oil Chemists Society, Rothgeb, T. M., Goodlander, B. D., Garrison, P. H., and Smith, L. A. (1988).

EXAMPLE 1a

Isolation and Purification of *Bacillus* strain

The *Bacillus clausii* strain (DSM Accession No.: DSM 13585) was isolated from a soil sample collected in Sedona, Ariz., USA. The soil was spread upon the surface of an agar plate with TY-agar (see below) and 0.1 M sodium sesquicarbonate and colonies arising after incubation for 2 days at 37° C. were re-isolated and the pure culture was transferred to 500 ml shake flasks with 100 ml PS-1 medium (see below) and 0.1 M sodium sesquicarbonate.

The shake flasks were incubated for 4 days at 30° C. on a rotating table at 300 rpm. Subsequently, the subtilase was harvested and purified (see Example 1b below).

| TY-agar: | |
|---|---|
| Trypticase | 20 g |
| Yeast extract | 5 g |
| $FeCl_2$, 4 $H_2O$ | 0.6 ml of a 1% solution (w/v) |
| $MnCl_2$, 4 $H_2O$ | 0.1 ml of a 1% solution (w/v) |
| $MgSO_4$, 4 $H_2O$ | 1.5 ml of a 1% solution (w/v) |
| Destilled water | 1000 ml |
| Merck agar | 20 g |

The pH was adjusted to 7.3 with 4 N KOH before autoclaving for 20 minutes.

| PS-1 medium: | |
|---|---|
| Saccharose | 100 g |
| Soy bean flour | 40 g |
| $Na_2HPO_4$, 12 $H_2O$ | 10 g |

-continued

PS-1 medium:

| Pluronic PE 6100 | 0.1 ml |
| Tap water | 1000 ml |

The ingredients were mixed and homogenised. 100 ml medium was then filled into 500 ml baffled shake flasks and autoclaved.

EXAMPLE 1b

Isolation and Purification of the Subtilase

Approximately 1.6 liters of fermentation broth (from Example 1a) were centrifuged at 5000 rpm for 35 minutes in 1 liter beakers. The supernatants were adjusted to pH 7 using 10% acetic acid and filtered through a Seitz Supra S100 filter plate.

At room temperature, the filtrate was applied to a 100 ml Bacitracin agarose affinity column (Upfront Chromatography ANS) equilibrated with 0.01 M dimethylglutaric acid, 0.1 M boric acid and 0.002 M calcium chloride adjusted to pH 7 with sodium hydroxide (Buffer A). After washing the column with Buffer A to remove unbound protein, the subtilase was eluted from the Bacitracin column using Buffer A supplemented with 25% 2-propanol and 1 M sodium chloride.

The fractions with protease activity from the Bacitracin purification step were combined and applied to a 750 ml Sephadex G25 column (Amersham Pharmacia Biotech) equilibrated with Buffer A.

Fractions with proteolytic activity from the Sephadex G25 column were combined and the pH was adjusted to pH 6 with 10% acetic acid and applied to a 150 ml CM Sepharose CL 6B cation exchange column (Amersham Pharmacia Biotech) equilibrated with a buffer containing 0.01 M dimethylglutaric acid, 0.1 M boric acid, and 0.002 M calcium chloride adjusted to pH 6 with sodium hydroxide.

The subtilase was eluted using a linear gradient of 0–0.2 M sodium chloride in 2 liters of the same buffer. Finally, the protease containing fractions from the CM Sepharose column were combined and filtered through a 0.2µ filter.

EXAMPLE 1c

Determination of Sequence

The DNA coding for the subtilase of the invention has been multiplied from DNA isolated from a Bacillus clausli HSB10 strain (DSM Accession No.: DSM 13585) by PCR using oligonucleotides with homology to the aprH309 gene of B. clausii NCIB 10309 described in WO 89/06279. (25 cycles of PCR were carried out with denaturation temperature for 60 seconds at 92° C., annealing for 30 seconds at 58° C., and elongation for 90 seconds at 72° C.).

The N-terminal primer (5'-AAT AGA GCT CAC CAG CTT GGA CM GTT GG-3' (SEQ ID NO:5)) anneal 20 to 40 basepair upstream for the ATG start codon and the C-terminal primer (5'-TTT GGA TCC ATA CAC AM AM ACG CTG TGC CC-3' (SEQ ID NO:6)) anneal 30 to 50 bp downstream for the TM stop codon.

The DNA and protein sequences were deduced from the PCR segment (SEQ ID NOS. 1 and 2).

EXAMAPLE 1d

Expression in B. clausii

The expression of the subtilase of the invention was optimised by inserting the pro- and mature part of the gene in frame with the signal sequence of the aprH309 gene of B. clausii (formerly B. lentus) (WO 89/06279) in the chromosome on a derivative of Bacillus clausii NCIB 10309. The integration was made in such a way that the pro sequence and the mature part of the original apr gene were deleted from the B. clausii chromosome and replaced by the pro sequence and the mature part of the gene encoding the enzyme of the invention.

By flanking the new apr gene with DNA fragments of the aprH309 gene the insertion into the chromosome was made. The two DNA segments from aprH309 consist of 500 bp directly upstream for the signal cutting site (in frame with the pro sequence of the enzyme of the invention) and 500 bp directly below the TM stop codon. The subtilase segment flanked by the two 500 bp aprH309 sequences was inserted into a cat derivative of the temperature sensitive pE194 plasmid. This recombinant plasmid was transformed by protoplast transformation to B. clausii (Akamatzu, T et all. Agric. Biol. Chem. 1984 vol 48: p.651–655) (The pH in the HCP 1.5 regeneration plates was adjusted to pH 9 by addition of sodium carbonate buffer to 0.05M). After regeneration of the B. clausii transformants the plasmid was inserted into the chromosome by homologous recombination at 48° C. selecting for resistance to 10 microgram/ml chloramphenicol. By lowering the temperature to 30° C. without chloramphenicol selection the plasmid will occasionally be lost from the chromosome leaving the subtilase inset behind. Among colonies with protease phenotype and without resistance towards 10 microgram/ml chloramphenicol cells was isolated and analysed and selected by PCR with specific primers for the subtilase gene. By PCR with primer (5'-MT AGA GCT CAC CAG CTT GGA CM GTT GG-3' (SEQ ID NO:7)) and primer (5'-TTT GGA TCC ATA CAC AAA AAA ACG CTG TGC CC-3' (SEQ ID NO:8)) a DNA fragment covering the total coding region was made and sequenced. The deduced amino acid sequence was identical to the mature subtilase of the invention.

EXAMPLE 2

The "Model Detergent Wash Performance Test"

In order to asses the wash performance of subtilases in a standard detergent composition, standard washing experiments may be performed using the below experimental conditions:

| Detergent: | Model detergent |
| Detergent dosage | 4.0 g/l |
| pH | 10.1 |
| Wash time | 20 min |
| Temperature: | 30° C. |
| Water hardness: | 15° dH |
| Enzyme concentration: | 10 nm (in the detergent solution) |
| Test system: | 10 ml beakers with a stirring rod |
| Textile/volume: | 5 textile pieces (Ø 2.5 cm)/ 50 ml detergent solution |
| Test material: | WFK10N (egg stains) |

The composition of the model detergent is as follows:

| | |
|---|---|
| 6.2% | LAS (Nansa 80S) |
| 2% | Sodium salt of $C_{16}$–$C_{18}$ fatty acid |
| 4% | Non-ionic surfactant (Plurafax LF404) |
| 22% | Zeolite P |
| 10.5% | $Na_2CO_3$ |
| 4% | $Na_2Si_2O_5$ |
| 2% | Carboxymethylcellulose (CMC) |
| 6.8% | Acrylate liquid CP5 40% |
| 20% | Sodium perborate (empirical formula $NaBO_2.H_2O_2$) |
| 0.2% | EDTA |
| 21% | $Na_2SO_4$ |
| Water | (balance) | pH of the detergent solution is adjusted to 10.1 by addition of HCl or NaOH. Water hardness is adjusted to 15° dH by addition of $CaCl_2$ and $MGCl_2$ ($Ca^{2+}$:$Mg^{2+}$=4:1) to the test system. After washing the textile pieces are flushed in tap water and air-dried.

Measurement of the reflectance ($R_{subtilase}$) on the test material is performed at 460 nm using a Macbeth ColorEye 7000 photometer (Macbeth, Division of Kollmorgen Instruments Corporation, Germany). The measurements are performed accordance with the manufacturer's protocol.

In order to determine a blank value, a similar wash experiment is performed without addition of enzyme. The subsequent measurement of the reflectance ($R_{blank}$) is performed as described right above.

A reference experiment is then performed as described above, wherein the wash performance of Savinase® is tested. The subsequent measurement of the reflectance ($R_{savinase}$) is performed as described right above.

The wash performance is evaluated by means of the Performance Factor (P) which is defined in accordance with the below formula:

$$P = (R_{subtilase} - R_{blank}) - (R_{savinase} - R_{blank})$$
$$= (R_{subtilase} - R_{savinase}).$$

EXAMPLE 3

The "Ovo-Inhibition Assay"

The below inhibition assay is based on the principle that the subtilase to be tested will catalyse the hydrolysis of a peptide-pNA bond, thereby releasing the yellow pNA, which may conveniently be followed at 405 nm. The amount of released pNA after a given period of time is a direct measure of the subtilase activity. By carrying out such hydrolysis experiments with and without inhibitor, respectively, it is possible to obtain a quantitative measure for the degree to which a certain subtilase is inhibited.

| Reaction conditions: | |
|---|---|
| Enzyme concentration: | 0.0003 mg/ml |
| Conc. of trypsin inhibitor type IV-0: | 0.0015 mg/ml |
| Initial substrate concentration: | 0.81 mM |
| Reaction time: | 11 min |
| Assay temperature: | 25° C. |
| Assay pH: | 8.6 |
| Absorbance measured at: | 405 nm |

Assay Solutions:

Substrate solution (2 mM): 500 mg Suc-Ala-Ala-Pro-Phe-pNA is dissolved in 4 ml DMSO (200 mM). This solution is diluted 100 times with the buffer solution described below. The concentration of substrate in the resulting substrate solution is 2 mM.

Inhibitor solution (0.005 mg/ml): 5 mg trypsin inhibitor type IV-0 (Sigma T-1886) is dissolved in 10 ml water. This solution is dissolved 100 times with the buffer solution described below. The concentration of inhibitor in the resulting inhibitor solution is 0.005 mg/ml.

Enzyme solution (0.001 mg/ml): 1 mg enzyme is dissolved in 10 ml water. This solution is dissolved 100 times with the buffer solution described below. The concentration of enzyme in the resulting enzyme solution is 0.001 mg/ml.

Buffer solution (pH 8.6): 15.7 mg Tris is dissolved in an appropriate amount of water and 0.75 ml 30% (w/v) BRIJ (BRIJ 35 polyoxyethylenelaurylether, 30% (w/v), Sigma Cat. No. 430AG-6) is added. The pH is adjusted to 8.6 with 4 M NaOH and the solution is diluted to 1 liter with water.

Assay with Inhibitor 1 volume unit (e.g. 80 microliter) inhibitor solution is mixed with 1 volume unit (e.g. 80 microliter) enzyme solution in an appropriate reaction vessel (e.g. a spectrophotometer cell or a micro titer plate) and equilibrated at 25° C. for 15 min. 1.375 volume units (e.g. 110 microliter) substrate solution is added to the reaction vessel after which the absorbance at 405 nm is followed for 11 min (e.g. by measuring every $10^{th}$ or $30^{th}$ second). The slope of the absorbance curve is calculated using linear regression analysis. The slope of the absorbance curve is denoted $alpha_{inhibitor}$.

Assay Without Inhibitor 1 volume unit (e.g. 80 microliter) buffer solution is mixed with 1 volume unit (e.g. 80 microliter) enzyme solution in an appropriate reaction vessel (e.g. a spectrophotometer cell or a micro titer plate) and equilibrated at 25° C. for 15 min. 1.375 volume units (e.g. 110 microliter) substrate solution is added to the reaction vessel after which the absorbance at 405 nm is followed for 11 min (e.g. by measuring every $10^{th}$ or $30^{th}$ second). The slope of the absorbance curve is calculated using linear regression analysis. The slope of the absorbance curve is denoted alpha.

Blank 1 volume unit (e.g. 80 microliter) inhibitor solution is mixed with 1 volume unit (e.g. 80 microliter) buffer solution in an appropriate reaction vessel (e.g. a spectrophotometer cell or a micro titer plate) and equilibrated at 25° C. for 15 min. 1.375 volume units (e.g. 110 microliter) substrate solution is added to the reaction vessel after which the absorbance at 405 nm is followed for 15 min. These measurements are not used in the calculations, but merely serve as a control that no enzyme has been added to the buffer and/or substrate solution.

Calculation of Residual Activity (RA)

The residual enzyme activity (RA) is calculated according to the below formula:

RA=(alpha$_{inhibitor}$/alpha)×100%

Using the above test, the following results were obtained:

| Subtilase | RA (%) |
|---|---|
| SEQ ID NO:1 | 38 |
| Savinase ® | <5 |

As it appears, the subtilase according to the invention is inhibited to a much lesser extent than the structurally similar subtilase Savinase®.

Deposit of Biological Material

The following biological material has been deposited under the terms of the Budapest Treaty with the Deutsche Sammiung von Mikroorganismen und Zelikulturen GmbH, Mascheroder Weg 1 B, D-38124 Braunschweig, Germany, and given the following accession number:

| Deposit | Accession Number | Date of deposit |
|---|---|---|
| *Bacillius clausii* HSB10 | DSM 13585 | Jul. 5, 2000 |

The invention claimed is:

1. An isolated subtilase having an amino acid sequence which has at least 97% identity with the amino acid sequence of amino acids 1 to 269 of SEQ ID NO: 2.

2. A subtilase of claim 1 having an amino acid sequence which has at least 98% identity with the amino acid sequence of amino acids 1 to 269 of SEQ ID NO: 2.

3. A subtilase of claim 2 having an amino acid sequence which has at least 99% identity with the amino acid sequence of amino acids 1 to 269 of SEQ ID NO: 2.

4. A subtilase of claim 1, where the subtilase—when tested in the "Ovo-inhibition Assay"—has a residual activity of at least 15%.

5. A subtilase of claim 4, where the subtilase has a residual activity of at least 20%.

6. A subtilase of claim 5, where the subtilase has a residual activity of at least 25%.

7. A subtilase of claim 6, where the subtilase has a residual activity of at least 30%.

8. A subtilase of claim 7, where the subtilase has a residual activity of at least 35%.

9. An isolated subtilase, which comprises the amino acid sequence of amino acids 1 to 269 of SEQ ID NO: 2.

10. A subtilase of claim 9, which consists of the amino acid sequence of amino acids 1 to 269 of SEQ ID NO: 2.

11. A subtilase of claim 1 which is a modified subtilase comprising a modification of the sequence of amino acids from 1 to 269 of SEQ ID NO: 2, wherein the modification comprises a substitution, a deletion, and/or an insertion at one of the positions 27, 36, 56, 76, 87, 96, 97, 98, 99, 100, 101, 103, 104, 120, 123, 129, 131, 132, 133, 143, 159, 167, 170, 192, 194, 206, 217, 218, 222, 224, 232, 235, 236, 245, 248, 252 and 274, wherein the modified subtilase has subtilase activity and each position corresponds to a position in the amino acid sequence of the mature subtilisin BPN' set forth in SEQ ID NO: 9.

12. A modified subtilase of claim 11, wherein the modification comprises at least one modification selected from the group consisting of K27R, *36D, T56P, N76D, N87S, A97N, A98AS, A98AS, N99ND, N99NR, N99A, N99T, R101G, P103A, V104A, V104I, V104N, V104Y, D120H, N123S, P129K, P131H, A133P, A133D, A133E, T143K, *159D, *159E, Y167A, R 170S, A194P, Q206E, F217R, N218S, M222S, M222A, T244S, A232V, K235L, Q236H, Q245R, N248D, N252K and T274A.

13. A subtilase of claim 11, wherein the modification comprises
V104N+R101G, K27R+V104Y+N123S+T274A, N76D+V104A, R101G+P103A+V104I+*159D+A232V+Q236H+Q245R+N248D+N252K; or any other combination of the modifications K27R, N76D, R101G, P103A, V104I, V104A, V104N, V104Y, N123S, *159D, A232V, Q236H, Q245R, N248D, N252K and T274A.

14. A cleaning or detergent composition, comprising a subtilase of claim 1 and a surfactant.

15. A composition of claim 14, which additionally comprises an amylase, cellulase, cutinase, lipase, oxidoreductase, another protease, or a mixture thereof.

16. A method for cleaning or washing a hard surface or laundry, comprising contacting the hard surface or the laundry with a composition of claim 14.

17. A method for removal of egg stains from a hard surface or from laundry, comprising contacting tile egg stain-containing hard surface or the egg stain-containing laundry with a composition of claim 14.

18. A cleaning or detergent composition, comprising the subtilase of claim 9 and a surfactant.

19. A composition of claim 18, which additionally comprises an amylase, cellulase, cutinase, lipase, oxidoreductase, another protease, or mixture thereof.

20. A cleaning or detergent composition, comprising the subtilase of claim 10 and a surfactant.

21. A composition of claim 20, which additionally comprises an amylase, cellulase, cutinase, lipase, oxidoreductase, another protease, or mixture thereof.

22. A method for cleaning or washing a hard surface or laundry, comprising contacting the hard surface or the laundry with the composition of claim 18.

23. A method for removal of egg stains from a hard surface or from laundry, comprising contacting the egg stain-containing hard surface or the egg stain-containing laundry with the composition of claim 18.

24. A method for cleaning or washing a hard surface or laundry, comprising contacting the hard surface or the laundry with the composition of claim 20.

25. A method for removal of egg stains from a hard surface or from laundry, comprising contacting the egg stain-containing hard surface or the egg stain-containing laundry with the composition of claim 20.

26. A cleaning or detergent composition, comprising the subtilase of claim 11 and a surfactant.

27. A composition of claim 26, which additionally comprises an amylase, cellulase, cutinase, lipase, oxidoreductase, another protease, or mixture thereof.

28. A method for cleaning or washing a hard surface or laundry, comprising contacting the hard surface or the laundry with the composition of claim 26.

29. A method for removal of egg stains from a hard surface or from laundry, comprising contacting the egg stain-containing hard surface or the egg stain-containing laundry with the composition of claim 26.

\* \* \* \* \*

SEQUENCE LISTING

<160> NUMBER OF SEQ ID NOS: 9

<210> SEQ ID NO 1
<211> LENGTH: 1143
<212> TYPE: DNA
<213> ORGANISM: Bacillus clausii
<220> FEATURE:
<221> NAME/KEY: CDS
<222> LOCATION: (1)..(1140)
<223> OTHER INFORMATION:
<221> NAME/KEY: mat_peptide
<222> LOCATION: (334)..()
<223> OTHER INFORMATION:

<400> SEQUENCE: 1

```
atg aat aaa ccg ttg ggg aaa att gtc gca agc act gca cta ctt        45
Met Asn Lys Pro Leu Gly Lys Ile Val Ala Ser Thr Ala Leu Leu
    -110              -105                 -100 att tct gtc gct ttt agt tca tcg att gca tcg gct gct gaa gaa gca    93
Ile Ser Val Ala Phe Ser Ser Ser Ile Ala Ser Ala Ala Glu Glu Ala
     -95                  -90                  -85 aaa gaa aaa tac tta att ggc ttt aat gaa cag gaa gct gtc agt gag   141
Lys Glu Lys Tyr Leu Ile Gly Phe Asn Glu Gln Glu Ala Val Ser Glu
-80                   -75                  -70                -65 ttt gtc gaa caa gta gat gca aat aat gat gtc gcc gtt ctc tct gag   189
Phe Val Glu Gln Val Asp Ala Asn Asn Asp Val Ala Val Leu Ser Glu
                    -60                  -55                 -50 gaa gag gaa gtc gaa att gaa ctg ctt cat gag ttc gaa acc att ccc   237
Glu Glu Glu Val Glu Ile Glu Leu Leu His Glu Phe Glu Thr Ile Pro
              -45                  -40                 -35 gtt tta tca gta gag tta agc cca gaa gat gtg gat acg ctt gaa ctc   285
Val Leu Ser Val Glu Leu Ser Pro Glu Asp Val Asp Thr Leu Glu Leu
        -30                  -25                 -20 gat cca gcg att tct tac att gag gaa gat gta gaa gta tcg att atg   333
Asp Pro Ala Ile Ser Tyr Ile Glu Glu Asp Val Glu Val Ser Ile Met
   -15                  -10                  -5                -1 gct cag tct gtg cca tgg gga att agc cgt gtg caa gca cct gcc gcc   381
Ala Gln Ser Val Pro Trp Gly Ile Ser Arg Val Gln Ala Pro Ala Ala
1                  5                   10                  15 cat aac cgc gga gtg aca ggt tcc ggt gta aaa gtt gct gtt ctt gat   429
His Asn Arg Gly Val Thr Gly Ser Gly Val Lys Val Ala Val Leu Asp
                 20                  25                  30 aca ggc att tcc gcc cat cca gac tta aat atc cgc ggc ggt gct agc   477
Thr Gly Ile Ser Ala His Pro Asp Leu Asn Ile Arg Gly Gly Ala Ser
         35                  40                  45
```

```
ttt gtg aca ggc gag cca acg tat caa gat ggc aat gga cac ggc acg      525
Phe Val Thr Gly Glu Pro Thr Tyr Gln Asp Gly Asn Gly His Gly Thr
 50                  55                  60 cat gtg gca ggg acg att gcc gct tta aac aat tcg att ggc gtc ctt      573
His Val Ala Gly Thr Ile Ala Ala Leu Asn Asn Ser Ile Gly Val Leu
 65                  70                  75                  80 ggc gta gcg cct aat gct gaa cta tac gct gtt aaa gta tta gca gcc      621
Gly Val Ala Pro Asn Ala Glu Leu Tyr Ala Val Lys Val Leu Ala Ala
                 85                  90                  95 aac ggc aga ggc cca gtc agc tca att gcc caa ggg ttg gaa tgg gca      669
Asn Gly Arg Gly Pro Val Ser Ser Ile Ala Gln Gly Leu Glu Trp Ala
            100                 105                 110 gga aac aat ggc atg gac gtt gcc aac ttg agt tta gga agt cca tcg      717
Gly Asn Asn Gly Met Asp Val Ala Asn Leu Ser Leu Gly Ser Pro Ser
        115                 120                 125 cca agc gca acg ctt gag caa gcg gtt aat agc gct act tct aga ggc      765
Pro Ser Ala Thr Leu Glu Gln Ala Val Asn Ser Ala Thr Ser Arg Gly
    130                 135                 140 gtc ctt gtc gta gca gca act gga aac tca gga aca ggc tcc ctc gac      813
Val Leu Val Val Ala Ala Thr Gly Asn Ser Gly Thr Gly Ser Leu Asp
145                 150                 155                 160 tac cca gct cgt tat gcg aac gct atg gca gtc gga gct act gac caa      861
Tyr Pro Ala Arg Tyr Ala Asn Ala Met Ala Val Gly Ala Thr Asp Gln
                165                 170                 175 aac aac aac cgc gcc agc ttt tct cag tac gga gca ggg ctt gac att      909
Asn Asn Asn Arg Ala Ser Phe Ser Gln Tyr Gly Ala Gly Leu Asp Ile
            180                 185                 190 gtt gcg cca ggt gta aac gtg cag agc aca tac cca ggt tca act tac      957
Val Ala Pro Gly Val Asn Val Gln Ser Thr Tyr Pro Gly Ser Thr Tyr
        195                 200                 205 gct agc ttc aac ggt aca tcg atg gcg act cct cac gtt gtc ggt gta     1005
Ala Ser Phe Asn Gly Thr Ser Met Ala Thr Pro His Val Val Gly Val
    210                 215                 220 gca gcc ctt gta aaa caa aaa aac cca tct tgg tcc aat gta caa atc     1053
Ala Ala Leu Val Lys Gln Lys Asn Pro Ser Trp Ser Asn Val Gln Ile
225                 230                 235                 240 cgc aat cat cta aag aat aca gcc aca agt ttg ggt agc acg aac ttg     1101
Arg Asn His Leu Lys Asn Thr Ala Thr Ser Leu Gly Ser Thr Asn Leu
                245                 250                 255 tat gga agc ggg ctt gtc aat gca gaa gca gca aca cgc taa             1143
Tyr Gly Ser Gly Leu Val Asn Ala Glu Ala Ala Thr Arg
            260                 265

<210> SEQ ID NO 2
<211> LENGTH: 380
<212> TYPE: PRT
<213> ORGANISM: Bacillus clausii

<400> SEQUENCE: 2

Met Asn Lys Pro Leu Gly Lys Ile Val Ala Ser Thr Ala Leu Leu
            -110                -105                -100

Ile Ser Val Ala Phe Ser Ser Ile Ala Ser Ala Glu Glu Ala
    -95                 -90                 -85

Lys Glu Lys Tyr Leu Ile Gly Phe Asn Glu Gln Glu Ala Val Ser Glu
-80                 -75                 -70                 -65

Phe Val Glu Gln Val Asp Ala Asn Asn Asp Val Ala Val Leu Ser Glu
                -60                 -55                 -50

Glu Glu Glu Val Glu Ile Glu Leu Leu His Glu Phe Glu Thr Ile Pro
            -45                 -40                 -35
```

```
Val Leu Ser Val Glu Leu Ser Pro Glu Asp Val Asp Thr Leu Glu Leu
        -30                 -25                 -20
Asp Pro Ala Ile Ser Tyr Ile Glu Glu Asp Val Glu Val Ser Ile Met
        -15                 -10                  -5              -1
Ala Gln Ser Val Pro Trp Gly Ile Ser Arg Val Gln Ala Pro Ala Ala
 1               5                   10                  15
His Asn Arg Gly Val Thr Gly Ser Gly Val Lys Val Ala Val Leu Asp
             20                  25                  30
Thr Gly Ile Ser Ala His Pro Asp Leu Asn Ile Arg Gly Gly Ala Ser
         35                  40                  45
Phe Val Thr Gly Glu Pro Thr Tyr Gln Asp Gly Asn Gly His Gly Thr
     50                  55                  60
His Val Ala Gly Thr Ile Ala Ala Leu Asn Asn Ser Ile Gly Val Leu
 65                  70                  75                  80
Gly Val Ala Pro Asn Ala Glu Leu Tyr Ala Val Lys Val Leu Ala Ala
                 85                  90                  95
Asn Gly Arg Gly Pro Val Ser Ser Ile Ala Gln Gly Leu Glu Trp Ala
            100                 105                 110
Gly Asn Asn Gly Met Asp Val Ala Asn Leu Ser Leu Gly Ser Pro Ser
            115                 120                 125
Pro Ser Ala Thr Leu Glu Gln Ala Val Asn Ser Ala Thr Ser Arg Gly
            130                 135                 140
Val Leu Val Val Ala Ala Thr Gly Asn Ser Gly Thr Gly Ser Leu Asp
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
            195                 200                 205
Ala Ser Phe Asn Gly Thr Ser Met Ala Thr Pro His Val Val Gly Val
210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Ala Gly Lys Ala Leu
 1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic
```

-continued

```
<400> SEQUENCE: 4

Ala Gly Gly Leu
1

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
aatagagctc accagcttgg acaagttgg                                         29

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
tttggatcca tacacaaaaa aacgctgtgc cc                                     32

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
aatagagctc accagcttgg acaagttgg                                         29

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
tttggatcca tacacaaaaa aacgctgtgc cc                                     32

<210> SEQ ID NO 9
<211> LENGTH: 275
<212> TYPE: PRT
<213> ORGANISM: Bacillus

<400> SEQUENCE: 9

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
        50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95
```

-continued

```
Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
        130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
        210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```